United States Patent [19]

Callahan et al.

[11] Patent Number: 4,983,564

[45] Date of Patent: Jan. 8, 1991

[54] METHOD OF MAKING CROSSLINKED LAYERED COMPOUNDS

[75] Inventors: Kenneth P. Callahan, Cupertino; Martin B. Dines, deceased, late of Laguna Beach, both of Calif., by Elaine Dines, legal representative

[73] Assignee: Occidental Research Corporation, Los Angeles, Calif.

[21] Appl. No.: 885,244

[22] Filed: Jul. 14, 1986

Related U.S. Application Data

[63] Continuation-in-part of Ser. No. 614,111, May 24, 1984, abandoned.

[51] Int. Cl.$^5$ .................... B01J 31/00; B05D 7/00; B32B 3/06

[52] U.S. Cl. ................ 502/166; 71/64.11; 71/DIG. 1; 424/84; 424/405; 427/213.3; 427/213.33; 427/220; 428/402.24; 428/404; 502/162; 502/210; 502/211; 502/213; 514/965; 568/454; 568/456

[58] Field of Search ............ 252/315.2, 213.3, 213.33, 252/220; 428/402.24, 404; 106/308 Q, 450; 502/162, 166, 210, 211, 213

[56] References Cited

U.S. PATENT DOCUMENTS

| | | | |
|---|---|---|---|
| 3,674,709 | 7/1972 | Barrer et al. | 423/328 X |
| 4,098,736 | 7/1978 | Li et al. | 524/590 X |
| 4,176,090 | 11/1979 | Vaughan et al. | 502/63 |
| 4,216,188 | 8/1980 | Shabrai et al. | 423/118 |
| 4,384,981 | 5/1983 | Dines et al. | 502/167 |
| 4,386,013 | 5/1983 | Callahan et al. | 502/162 |
| 4,455,382 | 6/1984 | Wu | 106/308 Q X |

FOREIGN PATENT DOCUMENTS 2084166 4/1982 United Kingdom ............... 502/162

OTHER PUBLICATIONS

Jacobs: "Carboniogenic Activity of Zeolites", Elsevier Scientific Publishing Co., New York, 1977, p. 3.

Hydrothermal Chemistry of Zeolites, Barrer et al., Academic Press, 1982, pp. 8–11.

*Primary Examiner*—Richard D. Lovering
*Attorney, Agent, or Firm*—Robert J. Baran

[57] ABSTRACT

The instant invention relates to a method for converting phosphorus containing polymers from a two dimensional layered structure into a three dimensional structure by crosslinking such layers. The method and the resulting crosslinked polymers may be used to encapsulate active materials such as catalysts, pesticides, etc. by intercalating such active materials between the layers prior to crosslinking. Thus, the egress of said active materials into the environment during use may be hindered or prevented.

26 Claims, No Drawings

METHOD OF MAKING CROSSLINKED LAYERED COMPOUNDS

CROSSREFERENCE TO RELATED APPLICATIONS

This application is a continuation-in-part of U.S. Pat. Application Ser. No. 614,111, filed on May 24, 1984 and now abandoned, in the names of Callahan, et al.

BACKGROUND OF THE INVENTION

1. Field of the Invention

The instant invention relates to a method for converting phosphorus containing polymers from a two dimensional, layered structure into a three dimensional structure by crosslinking such layers. Preferably, the method and the resulting crosslinked polymers are used to encapsulate active materials such as catalysts, pesticides, etc. by intercalating such active materials between the layers prior to crosslinking. Thus, the egress of said active materials into the environment during use may be hindered or prevented.

2. Background of the Prior Art

Methods for encapsulating an active moiety are well known in the prior art. Such methods may comprise surrounding an active moiety, such as a drug, pesticide, etc., by a polymeric material. The encapsulated product can be designed to allow the active moiety to permeate through the capsule wall into the environment of use over a period of time (slow release) or the capsule can be utilized by abrupt rupture to release the active moiety into an environment immediately. The capsule can also be used by allowing a reactant to permeate through the wall for interaction with the active moiety within the capsule and the reaction products recovered by back permeation or immobilized inside the capsule. In general, the above described encapsulated products utilize a polymeric material functioning as a membrane to isolate the active moiety from environment or control the passage of the active moiety into the environment.

It is also known that various separations can be effected with materials having pores which are designed to admit the passage therethrough of molecules of less than a certain size while prohibiting the passage of larger molecules. For example, the crystalline aluminosilicates known as zeolites have been utilized for the separation of molecules on the basis of molecular size.

A novel class of compounds, has now become known, which compounds may be described as inorganic polymers. These compounds are described in U.S. Pat. Nos. 4,232,146; 4,235,990; 4,235,991; 4,256,872; 4,267,308; 4,276,409; 4,276,410; 4,276,411; 4,298,723; 4,299,943; 4,373,079; 4,384,981; 4,386,013; 4,390,690; 4,429,111; and 4,436,899 which are hereby incorporated by reference. These compounds may be prepared having a layered structure similar to the layered structure of zirconium phosphate. The above patents teach that these novel layered compounds have many uses. However, although these layered compounds may be formed with a "pillared" structure by synthesis from bifunctional acids comprising a Group V atom, it has nowhere been disclosed that such compounds may be converted from their normal two-dimensional (layered) structure into a three-dimensional structure, after synthesis, by crosslinking said layers.

Further, with reference to the preferred bisphosphonic acid crosslinking agents of the method of this invention (described below), it has been disclosed that monophosphonic acid esters may be exchanged into the above layered compounds after synthesis. However, the purpose of such exchange was to vary the pendant funtional groups within the layers; not to crosslink the layers and provide a three-dimensional structure.

Finally, U.S. Pat. Nos. 4,384,981 and 4,386,013 teach that the method of the instant invention may be utilized to prepare catalysts, such as hydrogenation and hydroformylation catalysts which are resistant to leaching. Such teaching, which is the invention of the inventive entity of the instant application, is hereby incorporated by reference to show one embodiment of the instant invention.

SUMMARY OF THE INVENTION

The instant invention provides a method of making layered compounds resistant to the egress or ingress of moieties greater than a specific size from or into the interlayer space. In one aspect, the instant invention provides a method for encapsulating an active moiety, such as, for example, a catalyst, a pesticide, etc., between the layers of certain layered compounds, and the products prepared by said method. The products can be designed, so that the active moiety is utilized by release into an environment over a period of time (slow release) or abruptly released by destruction of the layered compound. Alternatively, it may be desirable (if said active moiety is a catalyst) to retain said active moiety within said capsule during use. Both the method of making the layered compounds resistant to egress or ingress of said moieties as noted above and products including an active moiety encapsulated within the layered compounds are novel.

A novel method for making a product comprising an active moiety encapsulated within a layered compound comprises the steps of;

(a) intercalating an active moiety, e.g. a Group VIII metal or compound having catalytic activity, (or the precursor of an active moiety) into the layers of the layered compound, wherein said layered compound is characterized as a layered crystalline material comprising contiguous layers, of said layers being spaced from and substantially unconnected to its neighboring layer to thereby allow access of said active moiety, into the interior of said crystalline material, and (b) crosslinking said layers to thereby connect said contiguous layers to neighboring layers and hinder egress of said active moiety from the interior of said crystalline material.

DETAILED DESCRIPTION OF THE INVENTION

1. The Layered Compound

The compound useful in the products and method of the instant invention will be selected from the group consisting of compounds represented by the formula $M(O_3ZO_xR)_n$. In the above formula n varies from $>1$ to 2, more preferably from 1.1 to 2 and most preferably from 1.5 to 2, e.g. 2. M represents a tetravalent metal ion selected from the group consisting of

| Zr | Te | Pr | Mn |
| W | Sn | Pb | Ir |
| U | Si | Os | Hf |
| Ti | Ru | Nb | Ge |

| | -continued | | |
|---|---|---|---|
| Th | Pu | Mo | Ce |

Z is an atom selected from the group consisting of the members of Group V of the Periodic Table of the Elements having an atomic weight of at least 30; R is selected from the group consisting of hydrogen and organic radicals and x varies from 0 to 1. More preferably, said compound will be selected from the group consisting of the compounds represented by the general formula $M(O_3PR)_{2'}$ or $M(O_3POR)_{2'}$.

The above compounds may by be prepared by a process which comprises reacting, in a liquid medium, at least one acid compound, i.e. an organo-substituted, pentavalent atom containing acid, having the formula $$((HO)_2OZO_x)_kR$$

wherein k varies from 1 to <2 with at least one of the above tetravalent metal ions to precipitate a solid in which the molar ratio of pentavalent atom to tetravalent metal varies from 2 to 1, the pentavalent atom is covalently bonded to R and when x equals 1, R is linked to the pentavalent element Z through oxygen.

It should be noted that x will be 0 when the starting material for preparing the compound is represented by the general formula

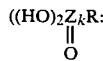

, e.g.,

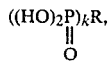

i.e., phosphorus acid or organophosphonic acids. When the starting material is represented by the general formula

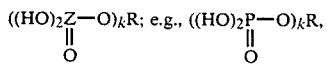

i.e., organophosphoric acids or phosphoric acid, x will be 1. If a mixture of such starting materials are used, x will vary from 0 to 1 in accordance with the ratio of the starting materials and n will vary from 1 to 2.

The tetravalent metal M and the pentavalent atom Z, may be selected in accordance with the desired properties for the active moiety by those skilled in the art. However, M is preferably Zr and Z is preferably P.

R is selected from the group consisting of hydrogen radicals, organo acyclic, alicyclic, heteroacyclic, heterocyclic, aromatic groups, and mixtures thereof. In one embodiment of this invention at least a portion of the R groups comprise a crosslinkable functional group.

R will be chosen to enable the compound to achieve a layered structure, whereby an active moeity may be intercalated within such layers. Thus, the size of the R may be important, since very bulky R groups may disrupt such layering.

In general, with phosphorus as the pentavalent atom, the organo group should occupy no more than about 24 $Å^2$ for proper spacing. This limitation is imposed by the basic crystal structure of zirconium phosphate. A spacing of 5.3 Å is known to exist between zirconium atoms in the zirconium plane of a crystal, and a total area of about 24 $Å^2$ is known for the space bounded by zirconium atoms. It follows that any group anchored on each available site cannot have an area much larger than the site area and maintain the layered structure.

This limitation can be avoided through the use of a combination of larger and smaller groups, i.e., mixed components. If some of the sites are occupied by groups which have an area much less than about 24 $Å^2$ adjacent groups can be larger than 24 $Å^2$ and still maintain the layered structure of the compound.

The cross-sectional area which will be occupied by a given organo group can be estimated in advance of actual compound preparation by use of CPK space filling molecular models (Ealing Company) as follows: A model for the alkyl or aryl chain and terminal group is constructed, and it is situated on a scaled pattern of a hexagonal array with 5.3 Å site distances. The area of the group is the projection area on this plane. Some areas which have been determined by this procedure are listed in Table 1.

TABLE I

| Moiety | Minimum Area ($Å^2$) | Moiety | Minimum Area ($Å^2$) |
|---|---|---|---|
| Alkyl chain | 15 | Isopropyl | 22.5 |
| Phenyl | 18 | t-Butyl | 25 |
| Carboxyl | 15 | Chloromethyl | 14 |
| Sulfonate | 24 | Bromoethyl | 17 |
| Nitrile | 9 | Diphenyl- phosphino | 50 (approx.) |
| Morpholinomethyl | 21 | Mercaptoethyl | 13.5 |
| Trimethylamino | 25 | | |

Note that the bulk of the above described moieties must also be included when calculating the correct R group size for attaining the preferred layered structure in the support.

At least a portion of the R groups may comprise a crosslinkable, functional group suitable for reaction with a multifunctional (preferably a bifunctional) crosslinking agent to convert the two dimensional, layered structure into a three dimensional structure. Suitable crosslinkable functional groups and bifunctional crosslinking agents suitable for reaction therewith are given in Table II, below.

TABLE II

| Functional Group | Bifunctional Crosslinking Agent |
|---|---|
| hydroxyl | bis carboxylic acids, bis phosphonic acids, etc. |
| carboxylic acid | dialcohols |
| epoxide | dialcohols, diamines, etc. |

Other crosslinkable functional groups and bifunctional crosslinking agents are known in the polymer arts and reed not be discussed further herein.

The functional group is preferably a terminal group for ease of reaction with the bifunctional crosslinking agent and, for efficient crosslinking, the molecular size of the bifunctional crosslinking agent is at least sufficient to bridge the interlayer space between functional groups pendant from adjacent layers.

The preferred functional groups are selected from the group consisting of carboxylic acid and hydroxyl groups and the preferred bifunctional crosslinking agents are selected from the corresponding bifunctional crosslinking agents listed in Table II above.

2. The Active Moiety

The active moiety may be selected from compounds that are desirably released into the environment over a period of time (slow release) or abruptly (by rupture or other rapid disintegration of the physical integrity of the layered compound), or compounds that are desirably retained in an encapsulated state during use. Examples of moieties which are desirably released slowly into the environment include fertilizers, e.g. nitrogen, phosphorous, and potassium compounds such as urea, urea-formaldehyde derivatives, etc.; micronutrients for plants and animals such as vitamins; pharmaceuticals, such as antibiotics, antihistamines, antipyretics, etc.; pesticides, such as insecticides, e.g. methylparathion, diazinon, endosulfan etc.; herbicides, e.g. propanil, atrazine, propachlor, etc.; rodenticides, e.g. zinc phosphide, thallium sulfate, etc.; fungicides and nematocides e.g. dichloropropene, 1,2-dibromoethane, methylisothiocyanate, etc.; perfumes, including insect attractants such as (Z)-9-dodecen-1-ol acetate, (Z)-7,8-epoxy-2-methyl octadecane, etc.; stabilizers; etc. Examples of active moieties which are desirably abruptly released into the environment by controlled disintegration of the layered compound include coreactants which must be mixed just prior to use, e.g. epoxy adhesives, solvent activated adhesives, dyes, flavors, etc. (These and other coreactive systems are illustrated in U.S. Pat. No. 4,098,736, herein incorporated by reference.)

Examples of active moieties which are desirably encapsulated during use include catalysts for various chemical reactions, including both heterogenous and homogeneous catalysts. For example catalysts used in hydrocarbon conversions and other chemical reactions such as hydrogenation, dehydrogenation, oxidation, cyclization, isomerization, polymerization, cracking, alkylation, etc., as known in the art, are conveniently utilized as the active moiety. Examples of such catalysts include transition metal complexes, e.g. alkenyl, carbonyl, nitrilo, halide, and phosphino complexes of palladium, aluminum, titanium, cobalt, rhodium, molybdenum, iridium, platinum, iron, ruthenium etc., which are used in, e.g. the synthesis of vinyl acetate from ethylene, hydrocarbonylation of alkenyls, carbonylation of methanol, syntheses of polyhydric alcohols from CO and $H_2$, stereospecific polymerization of $\alpha$-olefins; oxidation catalysts such as copper, platinum, vanadium, etc., which are used in the oxidation of $NH_3$, CO and $SO_2$ etc.; mixed metal oxide catalysts, e.g. the combination of a transition metal oxide, e.g. $MoO_3$, $Fe_2O_3$, etc., and an oxide of a Group Va element, e.g. $Sb_2O_5$ and $Bi_2O_3$ which may be used for the ammoxidation of propylene; copper chloride utilized as a catalyst for the oxychlorination of ethylene; Fischer-Tropsch catalysts such as iron, ruthenium, rhodium, osmium, rhenium, etc.; methanation catalysts, e.g. ruthenium, nickel, cobalt, iron, etc.

The method of this invention is especially applicable to encapsulating catalysts comprising a noble metal, e.g. a Group VIII noble metal, i.e., platinum, palladium, iridium, ruthenium, etc., to prevent loss of the catalyst metal by leaching or deactivation by contacting with catalyst poisons included in a reactant-containing fluid.

The only limitation on the active moiety that may be encapsulated by the method of the instant invention is one of size. That is, the molecular dimensions of the active moiety must be suitable for intercalation between the layers of the layers of the layered compounds. The available interlayer spacing has been discussed above.

In general, at least one dimension of the active moiety should not exceed 24Å, unless a portion of smaller diluent groups, as mentioned above, is present and allows incorporation of a molecule having a larger dimension. (see next page)

The preferred active moiety comprises a Group VIII metal-containing hydroformylation or hydrogenation catalyst. The Group VIII metal or Group VIII metal compound may be selected from the group consisting of nickel, cobalt, platinum, palladium, rhodium, iridium, iron, ruthenium, osmium. These materials may be active either as the compound or the metal form. For example, various complex salts including halogen salts of Group VIII metals are useful as hydrogenation catalysts and for other catalytic reactions e.g. hydrocarbon conversion, etc. Other examples of useful Group VIII metal salts include carboxylates, nitrates, sulfates, $\beta$-diketonates, etc.

The Group VIII metal may also be provided as a complex wherein the Group VIII metal exists in the zero valence state, for example, carbonyl complexes, and various other complexes such as phosphines, nitriles, isonitriles, etc. of Group VIII metals are known hydrogenation moieties.

In general, any known catalyst, having the required size limitation, may be composited with the above layered compounds to provide novel catalysts.

Preferably, the Group VIII metal is selected from the group consisting of rhodium, palladium and platinum as either the metal or salt form. Most preferably, the active moiety is rhodium metal or rhodium chloride salt or complex.

3. Preparation of a Crosslinked Three Dimensional Structure

The preparation of the crosslinked, three dimensional structures of the instant invention may be illustrated by the preparation of a hydroformylation catalyst. However, this method is applicable to the preparation of three dimensional, crosslinked structures comprising any of the above active moieties and to three dimensional, crosslinked structures that do not include an active moiety. (The crosslinked layered compounds prepared according to the method of this invention, like the pillard layered compounds, disclosed in the prior art, are useful for the separation of molecules according to size.)

The above layered compound may be contacted with a solution comprising the active hydroformylation moiety, i.e., the Group VIII metal or Group VIII metal compound or a precursor thereof, for a time sufficient to enable such hydroformylation moiety to intercalate into the layers of such support compound. The solvent for dissolving said hydroformylation moiety or precursor may be aqueous or nonaqueous, since in general the layered compound is stable to both types of solvents. The layered compounds are unstable in the presence of aqueous alkali; therefore, solutions having a pH of at most 8 should be utilized for preparing the hydroformylation catalyst.

The intercalated layered compound may be separated from said Group VIII metal or Group VIII metal compound or precursor containing solution and excess solvent removed by filtration, then drying at a temperature of from about 25° to about 200° C. for a time sufficient to remove substantially all of said excess solvent. Drying may take place in air or an inert atmosphere or under vacuum. The layers are then crosslinked to thereby connect contiguous layers and provide a three-dimensional structure sufficient to hinder egress of said Group VIII metal or compound (or precursor thereof) from the interior of the layered compound.

The crosslinking may be carried out by contacting the intercalated compound with a bifunctional crosslinking agent adapted to react and form a covalent or electrostatic bond with a functional group of the pendant R group or a bis acid e.g. a bisphosphonic acid, in solution e.g. an aqueous solution, may be contacted with the intercalated compound for a time and at conditions sufficient to effect exchange of some of the interlayer R or O—R groups of layered compound for the bis acid. Conveniently the contacting may be effected at ambient temperature and pressure.

The intercalated layered compound may be activated for hydroformylation by contacting said dried catalyst with a reducing atmosphere, e.g., hydrogen gas, at room temperature or an elevated temperature of from about 25° C. to 200° C., preferably from about 50° C. to about 150° C., for a time sufficient to convert said Group VIII metal compound or precursor into an active hydroformylation moiety, e.g., a Group VIII metal.

Preferably the crosslinking is effected by means of a bis acid compound such as a bis acid having the general formula

wherein Z is as described above, x' is 0 or 1, and R' is an organo radical such as the organo radicals described above. More preferably Z is P and x' is 0. The ratio of the bifunctional crosslinking agent to the pendant functional groups may be selected to provide a highly or lightly crosslinked structure. For example, in lightly crosslinked structures only pendant groups near the edges of the adjacent layers may be crosslinked, while in highly crosslinked structures some or many of the interior pendant functional groups may be crosslinked. The desired degree of crosslinking will depend on the use of the crosslinked layered compound and may be determined by simple testing. If a relatively rapid release of an active moiety (or a large pored structure) is desired, light crosslinking is preferred.

The following are specific examples of the instant invention. There is no intention that the scope of the instant invention be limited to the examples, since there are many variations thereon which are within the ordinary skill of the art.

EXAMPLE 1

Preparation of "Jail-celled", Intercalated Rhodium Catalyst

A suspension of 0.353 g of the intercalation product of $Zr(O_3PC_2H_5)_{4/3}(O_3P(CH_2)_3P(C_6H_5)_2)_{2/3}$ and $RhCl(CO)(P(C_6H_5)_3)_2$, 2.360 g of 1,6-hexanediolbis-(6-phosphonohexanoate), 50 ml water and 10 ml acetonitrile was prepared and heated to reflux for 110 minutes, then (cooled, filtered, and washed with 3×20 ml acetone, followed by 2×20 ml diethyl ether. Infrared analysis of the solid showed a strong absorption at 1750 cm$^{-1}$ assigned to the ester carbonyl group. It is believed that a crosslinking reaction occurred at the edges of the layered solid support, which reaction served to decrease the leaching of rhodium from the catalyst support. A similar reaction is believed to have occurred in Example 2 below.

EXAMPLE 2

General Procedure for Hydroformylation

Catalyst (ca.0.2 g)) was suspended in 20 ml hexane in the glass liner of a Parr stainless steel bomb, then the reactor was assembled and sealed. The bomb was pressurized to 200 psi with CO and vented three times to remove ambient air. Propylene was then charged to its tank pressure (80 psig), followed by CO and $H_2$, each at 340 psig. The bomb was heated to 135° C. using the Parr heating mantle, and the bomb internal pressure was monitored with the attached gauge as a function of time. After 5–6 hours the reactor was cooled to room temperature, a gas sample was collected, the gas pressure was vented and the product mixture was separated from the catalyst by filtration. The liquid filtrate was analyzed by gas chromatography.

Catalytic runs were carried out using the exchanged rhodium catalyst of Example 7(a) and the pillared rhodium catalyst, of Example 5, of U.S. Pat. No. 4,386,013, and the 'jail-celled' rhodium catalyst of the above Example 1. The resulting product liquids were filtered through 0.2μ pore size paper to remove catalyst fines, and then analyzed for rhodium content. The results, presented in Table 2 indicate a substantial decrease in rhodium leaching when the pillared catalyst is used, and a further decrease when the "jail-celled" catalyst is used.

TABLE III

| RHODIUM CONTENT OF PRODUCT LIQUIDS | |
|---|---|
| Catalyst | Rhodium Content, mg/L |
| Exchanged rhodium | 35.7 |
| Pillared rhodium | 0.12 |
| Jail-celled exchanged rhodium | 0.07 |

Moreover, the 'jail-celled' catalyst showed an improvement in the ratio of linear to branched products as shown in Table IV, below

TABLE IV

| Catalyst | linear: branched |
|---|---|
| Exchanged Rhodium | 1.11* |
| Pillared rhodium | 0.82 |
| Jail Celled rhodium | 1.34 |

*Solvent used was toluene rather than hexane.

While particular embodiments of the invention have been described it will be understood, of course, that the invention is not limited thereto since many obvious modifications can be made and it is intended to include within this invention any such modifications as will fall within the scope of the appended claims.

What is claimed is:

1. A process for encapsulating an active moiety to hinder the egress of said active moiety into the environment which process comprises the steps of
   (a) intercalating an active moiety into the layers of a compound selected from the group consisting of compounds represented by the general formula:

$M(O_3ZO_xR)_n$ wherein M is a tetravalent metal; Z is a pentavalent atom; x varies from 0 to 1; R is a radical selected from the group consisting of hydrogen and organo radicals; and n varies from >1 to 2;

said compound being characterized as a layered crystalline material comprising contiguous layers, each of said layers being spaced from and substantially unconnected to its neighboring layer to thereby allow access of said active moeity into the interior of said crystalline material, and (b) crosslinking said layers to thereby connect said contiguous layers to neighboring layers and hinder egress of said active moiety from the interior of said crystalline material.

2. The process of claim 1 wherein at least a portion of R radicals comprise a crosslinkable functional group.

3. The process of claim 2 wherein said crosslinkable functional group is selected from the group consisting of hydroxyl, carboxylic and epoxide groups.

4. The process of claim 3, wherein said crosslinkable functional group is reacted with a bifunctioanl crosslinking agent selected from the group consisting of bis carboxylic acids, bisphosphonic acids, dialcohols, and diamines to crosslink said layers.

5. The product of claim 1

6. A process for preparing a catalyst comprising a moiety having catalytic activity intercalated between the layers of a layered crystalline material, said catalyst being characterized as resistant to egress of said moiety from between said layers, which process comprises the steps of:

(a) intercalating a moiety having catalytic activity into the layers of a compound selected from the group consisting of compounds represented by the general formula:

$M(O_3ZO_xR)_n$ wherein M is a tetravalent metal; Z is a pentavalent atom; x varies from 0 to 1; R is a radical selected from the group consisting of hydrogen and organo radicals; and n varies from >1 to 2;

said compound being characterized as a layered crystalline material comprising contiguous layers, each of said layers being spaced from and substantially unconnected to its neighboring layer to thereby allow access of said moiety into the interior of said crystalline material, and (b) crosslinking said layers to thereby connect said contiguous layers to neighboring layers and hinder egress of said moiety from the interior of said crystalline material.

7. The process of claim 6 which comprises crosslinking said layers by reacting said compound with a bis acid compound.

8. The process of claim 7 wherein said bis acid compound has the general formula:

$(HO)_2Z'O_{x'}R'O_{x'}Z'(OH)_2$ wherein Z' is a pentavalent element, x' is 0 or 1, and R' is an organo radical.

9. The process of claim 8 wherein Z' is P and x' is 0.

10. The process of claim 6 wherein M is selected from the group consisting of Zr, W, U, Ti, Th, Te, Sn, Si, Ru, Pu, Pr, Pb, Os, Nb, Mo, Mn, Ir, Hf, Ge, Ce and mixtures thereof.

11. The process of claim 10 wherein said moeity comprises a Group VIII metal or Group VIII metal compound.

12. The process of claim 11 wherein said Group VIII metal is selected from the group consisting of Pt, Ru, Pd, and Ir.

13. The process of claim 12 wherein said layers are crosslinked by reacting said compound with a bis acid compound having the general formula:

$(HO)_2ZO_{x'}R'O_{x'}Z(OH)_2$ wherein Z' is a pentavalent element, each x' is independently 0 or 1, and R' is an organo radical.

14. The process of claim 13 wherein R' is the radical $(CH_2)_5CO(CH_2)_6OC(CH_2)_5$ 15. The process of claim 14 wherein said compound comprises $Zr(O_3PC_2H_5)_{4/3}(O_3P(CH_2)_3P(C_6H_5)_2)_{2/3}$ 16. The process of claim 6 wherein at least a portion of a R radicals comprise a crosslinkable functional group.

17. The process of claim 16 wherein said crosslinkable functional group is selected from the group consisting of hydroxyl, carboxylic and epoxide groups.

18. The process of claim 17 wherein said crosslinkable functional group are reacted with a bifunctional crosslinking agent selected from the group consisting of bis carboxylic acids, bisphosphonic acids, dialcohols, and diamines to crosslink said layers.

19. The product of claim 6.

20. A process for preparing a layered crystalline material characterized as resistant to egress or ingress of moieties greater than a specific size from or into the layers thereof, which process comprises the step of:

(a) crosslinking a compound selected from the group consisting of compounds represented by the general formula:

$M(O_3ZO_xR)_n$ wherein M is a tetravalent metal, Z is a pentavalent atom, x varies from 0 to 1, R is selected from the group consisting of hydrogen and organo radicals, and n varies from >1 to 2, said compound being characterized as crystalline material comprising contiguous layers, each of said layers being spaced from and substantially unconnected to its neighboring layer at a distance sufficient to allow access of said moiety into the interior of said crystalline material, to thereby connect said neighboring layers and hinder egress or ingress of said moiety from or into the interior of said crystalline material.

21. The process of claim 20 wherein M is selected from the group consisting of Zr, W, U, Ti, Th, Te, Sn, Si, Ru, Pu, Pr, Pb, Os, Nb, Mo, Mn, Ir, Hf, Ge, Ce and mixtures thereof.

22. The process of claim 20 which comprises cross-linking said layers reacting said compound with a bis acid compound.

23. The process of claim 22 wherein said bis acid compound has the general formula:

$$(HO)_2Z'O_{x'}R'O_{x'}Z'(OH)_2$$

wherein Z' is a pentavalent element, x' is 0 or 1, and R' is an organo radical.

24. The process of claim 23 wherein Z' is P and X' is O.

25. The process of claim 23 wherein R' is the radical $$(CH_2)_5\overset{O}{\underset{\|}{C}}O(CH_2)_6O\overset{O}{\underset{\|}{C}}(CH_2)_5$$

26. The process of claim 25 wherein said compound comprises $$Zr(O_3PC_2H_5)_{4/3}(O_3P(CH_2)_3P(C_6H_5)_2)_{2/3}$$

* * * * *